United States Patent [19]

Semmlow et al.

[11] Patent Number: 5,109,863

[45] Date of Patent: May 5, 1992

[54] NONINVASIVE DIAGNOSTIC SYSTEM FOR CORONARY ARTERY DISEASE

[75] Inventors: John L. Semmlow, New Brunswick; Walter Welkowitz, Metuchen; John B. Kostis, Warren; Vasant Padmanabhan, Piscataway, all of N.J.

[73] Assignees: Rutgers, The State University of New Jersey, New Brunswick; University of Medicine and Dentistry of New Jersey, Newark, both of N.J.

[21] Appl. No.: 696,185

[22] Filed: May 6, 1991

Related U.S. Application Data

[62] Division of Ser. No. 426,770, Oct. 26, 1989, Pat. No. 5,036,857.

[51] Int. Cl.$^5$ .............................................. A61B 5/02
[52] U.S. Cl. ..................................... 128/715; 310/329
[58] Field of Search ............... 128/715, 680, 670; 364/413.03; 73/517 AV, 517 R; 310/329

[56] References Cited

U.S. PATENT DOCUMENTS

| | | | |
|---|---|---|---|
| 2,270,167 | 4/1939 | Meissner et al. | 128/715 |
| 2,722,614 | 8/1951 | Fryklund | 310/329 |
| 2,928,668 | 3/1960 | Blasingame | 73/517 A V |
| 2,963,911 | 12/1960 | Courtney-Pratt et al. | 73/517 R |
| 3,113,223 | 12/1963 | Smith et al. | 310/329 |
| 3,120,622 | 2/1964 | Dranetz et al. | 73/517 R |
| 3,479,536 | 11/1969 | Norris | 310/323 |
| 3,528,297 | 9/1970 | Lee | 73/517 R |
| 3,893,342 | 7/1975 | Florian et al. | 73/517 R |
| 4,220,160 | 9/1980 | Kimball et al. | 128/715 |
| 4,258,229 | 3/1981 | Eggert et al. | 128/773 |
| 4,428,381 | 1/1984 | Hepp | 128/715 |
| 4,431,935 | 2/1984 | Rider | 73/504 |
| 4,446,873 | 5/1984 | Groch et al. | 128/715 |
| 4,467,326 | 8/1984 | Kolm et al. | 342/51 |
| 4,493,326 | 1/1985 | Hill et al. | 128/680 |
| 4,546,777 | 10/1985 | Groch et al. | 128/715 |
| 4,549,552 | 10/1985 | Groch et al. | 128/700 |
| 4,598,587 | 7/1986 | Dwyer et al. | 310/329 |
| 4,649,930 | 3/1987 | Groch et al. | 128/715 |
| 4,656,383 | 4/1987 | Albert | 310/329 |
| 4,672,976 | 6/1987 | Kroll | 128/715 |
| 4,680,708 | 7/1987 | Ambos et al. | 364/413.06 |
| 4,720,866 | 1/1988 | Elias et al. | 381/67 |
| 4,781,200 | 11/1988 | Baker | 128/670 |
| 4,784,154 | 11/1988 | Shirley et al. | 128/715 |
| 4,792,145 | 12/1988 | Eisenberg et al. | 128/715 |
| 4,803,986 | 2/1989 | Peel et al. | 128/385 |
| 4,862,361 | 8/1989 | Gordon et al. | 364/413.03 |

OTHER PUBLICATIONS

David W. Mortara, Ph.D. Raymond E. Ideker, M.D., James J. Bailey, M.D.; Computerized Interpretation of the Electrocardiogram: Jun. 1984; Reference pp. 5-17 (James Bailey, M.D., Editor, Jun. 1984).

(List continued on next page.)

Primary Examiner—Francis Jaworski
Assistant Examiner—George Manuel
Attorney, Agent, or Firm—Oliff & Berridge

[57] ABSTRACT

A method and system for non-invasively detecting Coronary Artery Disease. The method comprises analyzing the diastolic heart sounds detected from a patient's chest cavity during the diastolic portion of the heart cycle in order to identify a low level auditory component associated with turbulent blood flow in partially occluded coronary arteries. These diastolic heart sounds are modeled using advanced signal processing techniques such as Autoregressive (AR), Autoregressive Moving Averaging (ARMA) and Eigenvector methods, so that the presence of such an auditory component may be reliably indicated even under high noise conditions. The system includes an acoustic transducer, pulse sensor device, signal processor means and a diagnostic display. Additionally, the system includes a controller for automatically sequencing data collection, analysis and display stages, therefore requiring a minimum of operator interaction. The system further discloses a piezoelectric type low mass accelerometer for use as an acoustic transducer providing high sensitivity at the high frequencies necessary for detecting coronary artery disease, specifically between 300 to 1200 Hz. In addition, the system discloses a method for automatically identifying and isolating a diastolic segment of a heart sound recording through a "window" placement technique. A window is placed relative to the second heart sound and various criteria are implemented to evaluate the recording for artifacts, i.e., data due to breath sounds, stomach growls, external ambient noise.

4 Claims, 8 Drawing Sheets

OTHER PUBLICATIONS

Akay et al., "Analysis of Diastolic Heart Sounds Before and After Angioplasty" IEEE, EMBS 10th Int'l Conf., Nov. 1988.

Akay et al., "Autoregressive Modeling of Diastolic Heart Sounds", IEEE, EMBS 10th Int'l. Conf., Nov. 1988.

Ortiz, M., "Acoustical Noninvasive Diagnosis of Coronary Artery Disease", Proc. of 13th Ann. NE. Bieng. Conf., 1987.

Ortiz, M., "Non-Invasive Acoustical Diagnosis of Coronary Artery Disease", Thesis, May, 1987.

Ortiz et al., "Coronary Artery Disease: Noninvasive Diagnosis" 40th ACEMB Proceedings, Sep. 1987.

Vermarien et al., "The Recording of Heart Vibrations: A Problem of Vibration in Measurement . . . " Med. & Bioeng. & Comp., Mar. 1984.

Semmlow et al., "Coronary Artery Disease-Correlates Between Diastolic Auditory . . . '" IEEE Trans. in BME, vol. 34, Feb. 1983.

Schwartz et al., "Improved Phonocardiogram System Based on Acoustic Impedance Matching", Am. J. Physiol., 1980.

Semmlow et al., "Non-Invasive Diagnosis of Coronary Artery Disease by Enhanced Coronary . . . ", IEEE Frontiers of Eng. in Health, 1982.

Kosugi, "Detection and Analysis of Cranial Bruit", IEEE Transaction on BME, vol. BME-34, No. 3, Mar. 1987.

Makhoul, "Linear Prediction: A Tutorial Review" Proceed. of the IEEE, vol. 63 No. 4, Apr. 1975.

Fischer et al., "Comparative Evaluation of Cardiac Microphones", IEEE EMBS 10th Int'l Conf., Nov. 1988.

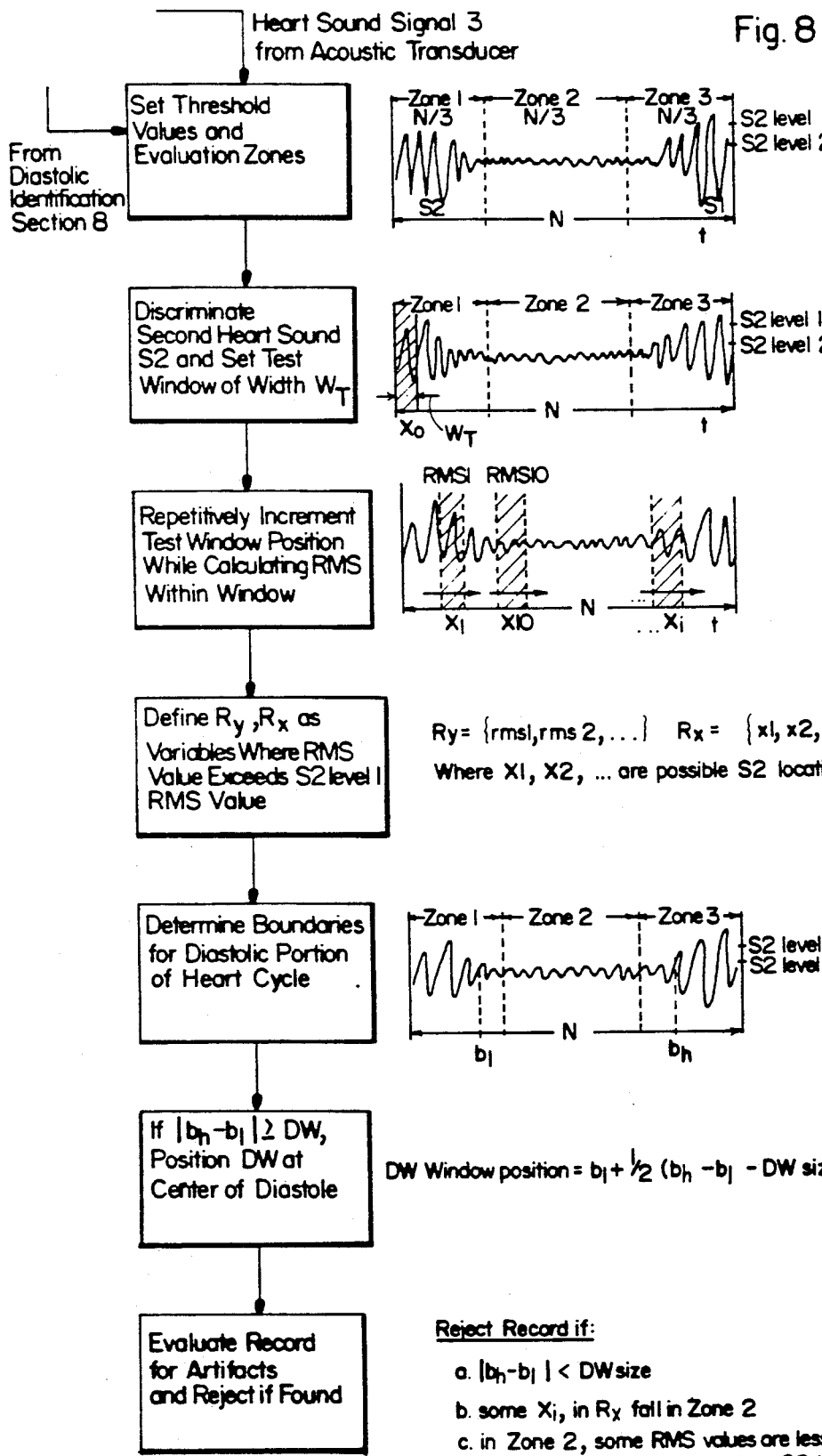

5,109,863

NONINVASIVE DIAGNOSTIC SYSTEM FOR CORONARY ARTERY DISEASE

This is a division of application Ser. No. 426,770, filed Oct. 26, 1989, now U.S. Pat. No. 5,036,857.

FIELD OF THE INVENTION

The present invention relates to a method and system for diagnosing coronary artery disease, and more particularly, a noninvasive method and system which affords reliable diagnostic information even in the early stages of coronary artery disease.

BACKGROUND

There are methods presently available for diagnosing coronary artery disease, each having its own advantages and disadvantages. The most definitive procedure is coronary angiography wherein a radio opaque dye is injected into the coronary arteries However, this procedure is invasive and presents a risk to the patient, and cannot be used routinely or for medical screening Another procedure involves the analysis of the electrical activity of the heart (the electrocardiogram or ECG) while under stress, to identify cardiac degradation resulting from an inadequate blood supply. While this method is noninvasive, it attempts to identify an effect of the disease, and therefore, it is not always reliable and cannot identify the disease in its early stages.

It has been found that coronary stenosis generates an auditory component due to turbulent blood flow in the partially occluded coronary arteries. Normally this auditory component is not present in a healthy patient. However, efforts in the past to detect this auditory component have met with limited success See J. Semmlow, W. Welkowitz, J. Kostis, and J. Mackenzie, "Coronary Artery Disease—Correlates Between Diastolic Auditory Characteristics and Coronary Artery Stenoses." IEEE Trans. Biomed. Engr., Vol. BME-30, No. 2, Feb. 1983. The auditory component associated with coronary stenosis is very weak and heavily contaminated with noise. Its detection by way of an acoustic transducer suffers from considerable attenuation due to the intervening heart tissue, the chest wall, and other compressible tissues such as lung or fat. In addition, its detection may be masked by the comparatively loud heart valve sounds as well as other naturally occurring body sounds or external ambient noise.

Previous efforts for isolating and detecting this low level auditory component have failed to provide results of sufficient reliability to accurately predict coronary stenosis. Previous techniques using traditional spectral methods such as the Fast Fourier Transform (FFT) could not provide sufficient resolution under such low signal to noise conditions. See M. Ortiz, J. Semmlow, J. Kostis and W. Welkowitz, "Coronary Artery Disease: Noninvasive Diagnosis." 40th ACEMB Proceedings, Sept. 1987.

The present invention noninvasively records and analyzes the heart sounds from a patient in order to reliably detect, among the other heart sounds, the presence of the auditory component associated with coronary stenosis. In the past, acoustic based systems have been employed to detect partial occlusions in other arteries such as the carotid or femoral arteries. However, these systems were only effective for detecting the relatively high level sounds from those arteries found in close proximity to the skin. These systems were not capable of reliably detecting the highly attenuated auditory component associated with partially occluded coronary arteries.

Also, in the past, phonocardiographic applications of parametric, or model-based, spectral analysis methods were utilized in the analysis of valve sounds for diagnosing valvular disorders. However, the analysis of these valve sounds again involved signal levels many times greater, and with correspondingly larger signal-to-noise ratios, than the auditory component associated with coronary stenosis which is sought to be identified in the present invention.

The present invention includes isolating the diastolic segment of a heart sound recording in order to more accurately analyze the auditory component of interest When analyzing heart sounds in the past, a diastolic time "window" was positioned using either the judgment of a human operator or automatic placement techniques. However, these previous windowing techniques often resulted in a misplaced window, or lacked editing features which would detect and reject artifacts due to breath sounds, stomach growls, external ambient noise, etc. Not surprisingly, such window misplacement and/or presence of artifacts often led to erroneous results, thus providing unreliable diagnostic information.

Additionally, the detection of heart sounds have been hindered in the past by the detrimental effects of existing acoustic transducers For example, mass loading by the acoustic transducer on the chest wall tended to attenuate and distort the recorded heart sounds. This attenuation typically increased as the load increased. To further complicate matters, the detrimental effect of loading became greater at the higher frequencies. Therefore, the detection of the low level sounds associated with coronary stenosis posed a serious problem, as the signals of interest have frequency components as high as 1.5 kHz. With the effect of mass loading, these highly attenuated signals could easily fall below the noise level and thus become undetectable Another obstacle associated with the acoustic transducer was that, typically, the prior art transducers and cardiac microphones had a flat frequency response with a high resonant frequency. This high resonance resulted in reduced sensitivity in the region of 300-1200 Hz, a region which has been found to be important in detecting sounds due to coronary artery stenosis Thus, there existed in the art a strong need for a noninvasive method and system for reliably diagnosing coronary artery disease based on detected heart sounds, even in the early stages of the disease. In addition, there existed a need for a method and system capable of reliable identification of a low level auditory component associated with coronary artery disease, especially in the presence of noise. Furthermore, there existed a need for a diastolic windowing technique for automatically isolating the diastolic segment of a heart sound recording and editing the segment for artifacts. In addition, there existed in the art a strong need for a low-mass acoustic transducer of sufficient sensitivity for detecting the low level auditory component associated with coronary artery disease.

SUMMARY OF THE INVENTION

Accordingly, the present invention has been developed to overcome the foregoing shortcomings by providing a system in which coronary artery disease may be detected both reliably and noninvasively.

It is therefore a primary object of this invention to provide reliable information to diagnose, or aid in a diagnosis of, coronary artery disease and to provide this information without discomfort or risk to the patient. Another object of this invention is to provide reliable information which is more indicative of coronary artery disease, particularly in the early stages, than other low risk diagnostic methods. Another object of this invention is to provide this information at low cost. Yet another object of this invention is to provide this information without the need for highly trained operating personnel.

In carrying these objects forward, this invention provides a system for detecting heart sounds from a patient's chest cavity, parametrically modeling the detected heart sounds in order to identify various frequency components within the heart sounds, detecting the presence of an auditory component in the heart sounds model which is associated with turbulent blood flow in a partially occluded coronary artery, and presenting diagnostic information based on the detected presence of the auditory component.

According to another aspect of this invention, signal processing techniques are provided which isolate the heart sounds produced in the chest to a selected portion of the cardiac cycle during which coronary blood flow is maximum.

In accordance to another aspect of this invention, additional signal processing techniques are provided to perform a window placement technique relative to a second heart sound in order to isolate the heart sounds occurring during the diastolic segment of the cardiac cycle. Additional signal processing techniques are provided whereby an evaluation for artifacts is performed on each diastolic segment, and a failure to meet one of several evaluation criteria will cause the record to be rejected.

According to another aspect of this invention, a low mass acoustic transducer apparatus is provided for detecting the very low level acoustic signals produced by coronary stenosis, even in the presence of background noise.

The application of this invention is as a medical device for diagnosing coronary artery disease. An operator attaches an acoustic transducer to the patient and initiates the analysis sequence. The system collects acoustic information over a sufficient number of cardiac cycles, analyzes the information and operates a display which provides diagnostic information concerning presence or absence of coronary artery disease.

These and other aspects and advantages of the present invention are described in or apparent from the following detailed description of the preferred embodiment.

BRIEF DESCRIPTION OF THE DRAWINGS

The preferred embodiment is described with reference to the drawings in which:

FIG. 8 shows a block diagram of the automatic diastolic window placement and editing procedure in accordance with the present invention.

DESCRIPTION OF THE PREFERRED EMBODIMENT

Figure 1:
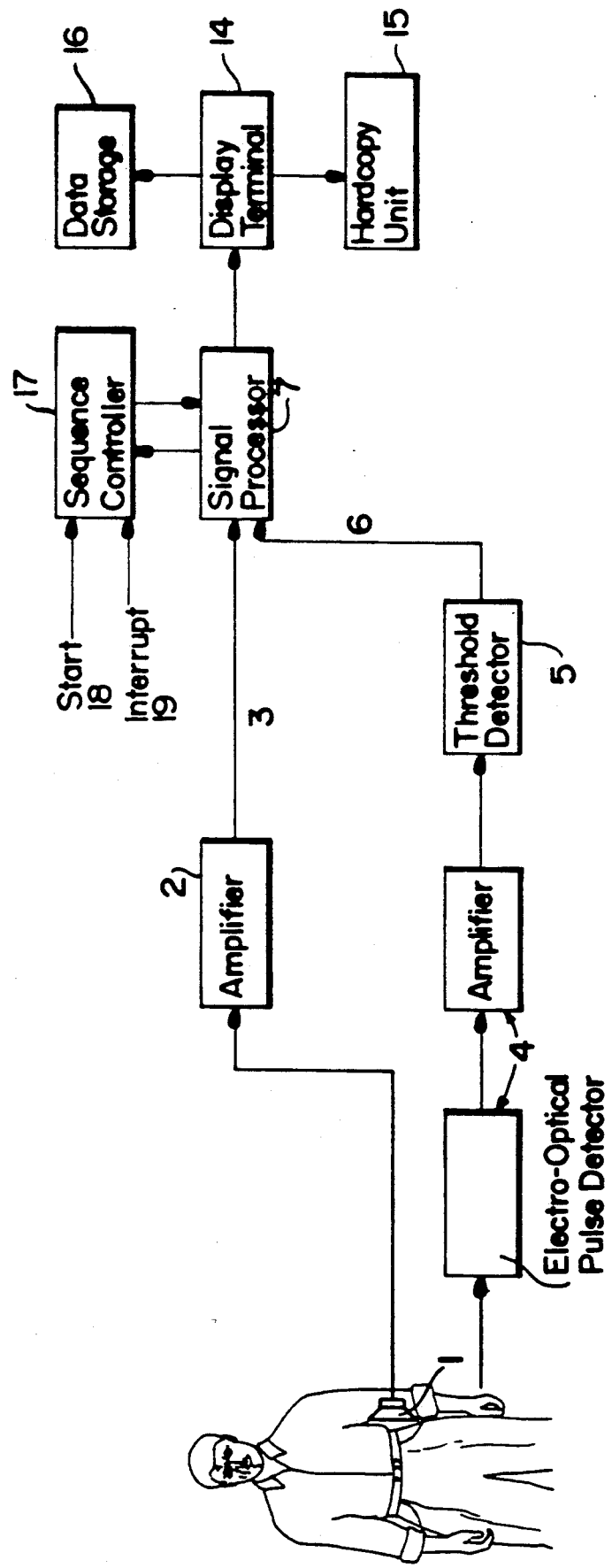
FIG. 1 is a block diagram of the diagnostic system in accordance with the present invention.

This invention is a diagnostic system for detecting the presence of partially occluded coronary arteries in a patient. The overall organization of the diagnostic system is seen in FIG. 1. The acoustic transducer 1 is coupled against the chest cavity of a patient using an ultrasonic acoustic gel. Heart sounds detected by the acoustic transducer 1 are then amplified by a conventional low noise audio amplifier 2, resulting in electrical heart sound signal 3.

Figure 2:
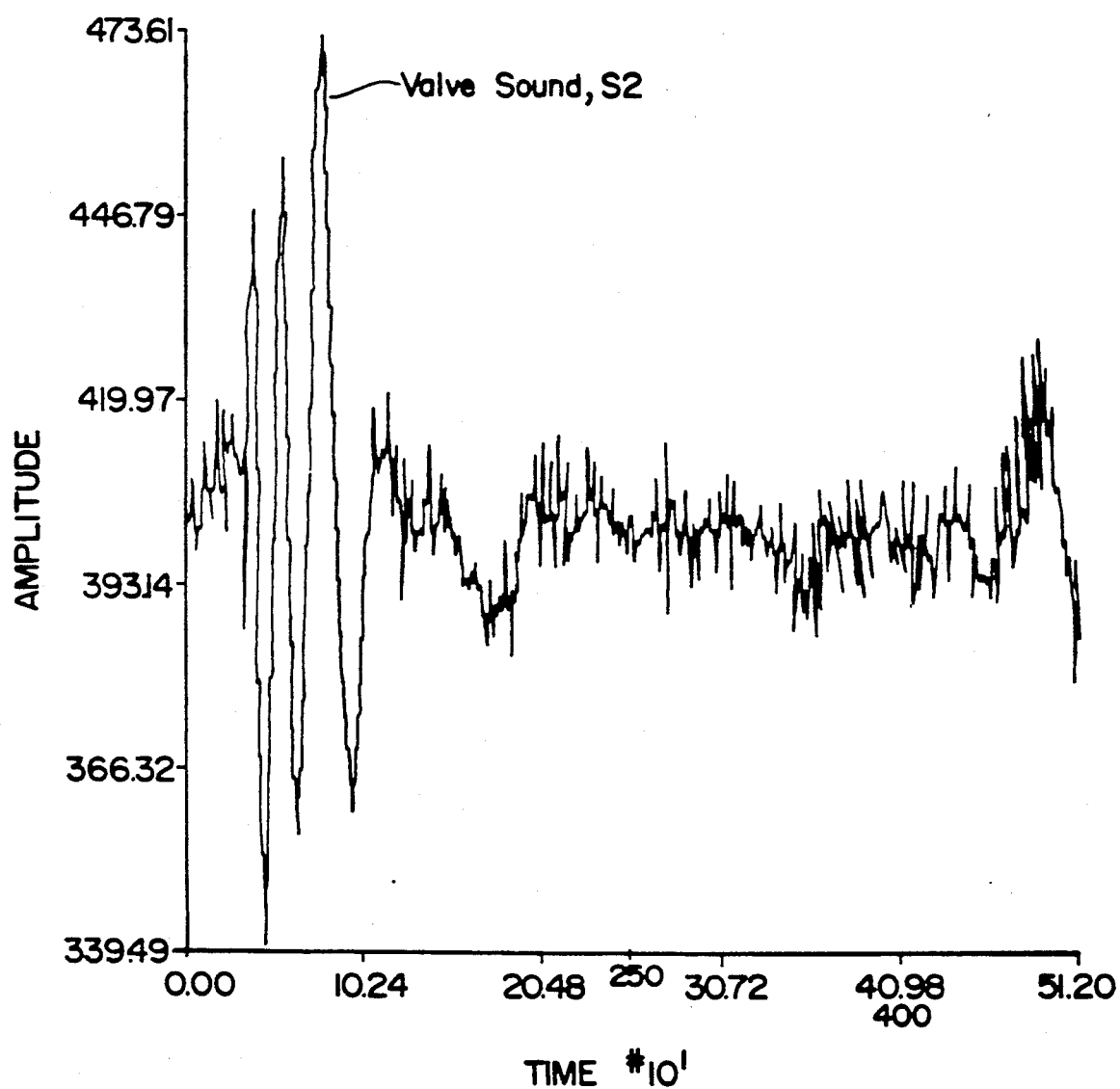
FIG. 2 is a diagram of a typical diastolic heart sound signal produced by the acoustic transducer showing valve sound S2 and sounds occurring during the subsequent diastolic period.

FIG. 2 shows a typical heart sound signal 3 as produced by the transducer 1 and amplifier 2. Heart sound signal 3 is similar to the standard phonocardiogram and includes sounds from the valves as well as other sounds in the chest cavity.

In the preferred embodiment of the present invention, a timing reference indicative of a particular point in the cardiac cycle is used in analyzing the detected heart sounds. FIG. 1 shows an electro-optical pulse detector which may be mounted to the finger of the patient. Electro-optical pulse detector and associated amplifier 4 provide an output signal based on the occurrence of the patient's pulse. The signal is processed through threshold detector 5 to provide timing reference signal 6 which is indicative of the occurrence of each pulse. In another embodiment, a standard ECG signal which is processed by a simplified QRS detector could be implemented in order to provide a similar timing reference 6 for the cardiac cycle.

Figure 3:
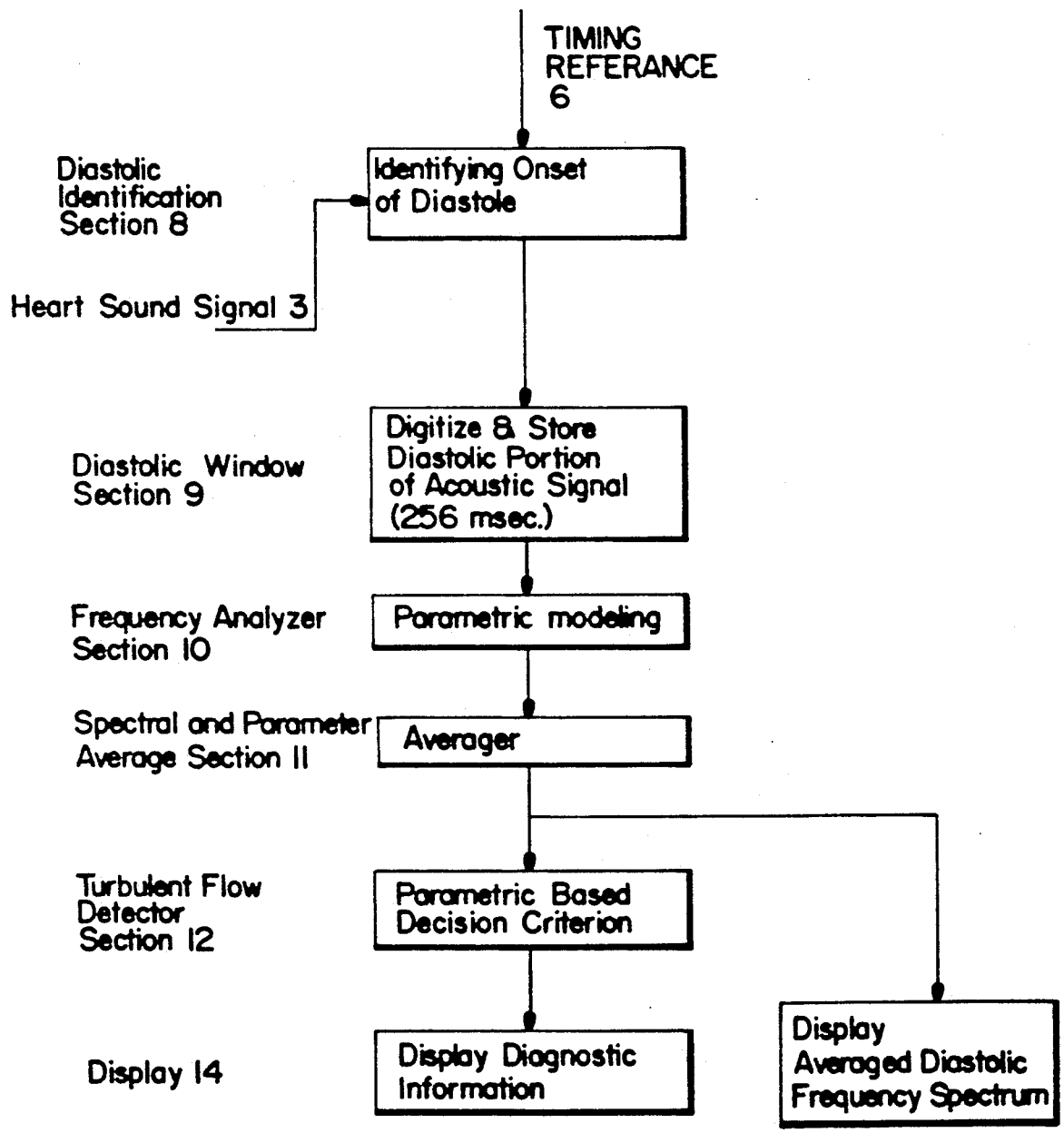
FIG. 3 is a block diagram of the signal processing and control section.

The heart sound signal 3 and timing reference signal 6 are coupled to signal processor 7 which performs subsequent analysis. FIG. 3 shows a detailed flow diagram of the signal processor 7 and controller 17. The signal processor 7 and controller 17 are preferably implemented using a standard microcomputer equipped with analog to digital conversion hardware. In another embodiment, all or a portion of the functions performed by the signal processor 7 and controller 17 sections could be implemented using equivalent electronic hardware.

The present invention analyzes primarily the diastolic portion of the cardiac cycle when attempting to identify the low level auditory component associated with coronary stenosis. Because these low level sounds are attributable to turbulent blood flow, they are likely to be loudest when coronary blood flow is at a maximum, that is, during the diastolic portion of the cardiac cycle. Therefore, the present invention preferably detects these low level sounds by analyzing only the heart sounds occurring during the diastolic portion of the cardiac cycle, and thereby avoiding the very loud first and second heart sounds associated with valve closure.

Using an automatic diastolic window placement technique described in detail below, diastolic window section 9 locates and isolates the diastolic segment of the heart sound signal 3 which occurs during the diastolic portion of the cardiac cycle. In the preferred embodiment, this diastolic window of the heart sound signal 3 is centered about the central portion of diastole and has a width of 256 msec. Diastolic window section 9 digitizes the diastolic segment of the heart sound signal 3 into 1024 samples, where $f_s = 4$ kHz. This digitized record y(n), of sounds occurring during diastole, is subsequently made available to frequency analyzer 10 for further spectral analysis.

According to the present invention, the spectral characteristics of y(n) must be examined to determine whether the auditory component associated with coronary artery disease is present in the recorded heart sound y(n). In order to do so, the frequency analyzer 10 models y(n) using parametric modeling methods which are described in detail below. These modeling methods must accurately define the diastolic frequency spectrum or other frequency parameters of y(n), such that, with the appropriate decision criterion, the presence of the auditory component associated with coronary stenosis may be reliably identified within the recorded heart sound.

The output from the frequency analyzer 10 is coupled to spectral and parameter averager 11 which averages the spectral or parametric characteristics of interest over 20 to 30 cycles. Such averaging improves the signal to noise ratio while, since it operates on the magnitude of a frequency domain signal, it also remains unaffected by slight shifts in the diastolic time window.

Thereafter, the modeled diastolic frequency spectrum or other frequency parameters are then sent from the averager 11 to the turbulent flow detector 12 for diagnostic analysis. The turbulent flow detector 12 applies one or more decision criteria to the y(n) model in order to identify the presence of the auditory component associated with coronary stenosis.

More specifically, once the frequency analyzer 10 utilizes parametric modeling techniques to construct and define the diastolic frequency spectrum or other parameters of y(n), the turbulent flow detector 12 then applies a predetermined decision criteria based on one or more of the model parameters. Thereby, the turbulent flow detector 12 identifies the presence of such an auditory component based on the known characteristics of these model parameters in a patient suffering from coronary artery disease.

The diagnostic information produced by the turbulent flow detector 12 is then sent to the display terminal 14 such as the CRT of a standard computer terminal. This information received from the turbulent flow detector 12 indicates the likelihood of coronary artery disease. A graph of the averaged diastolic frequency spectrum or a plot showing the location of the model zeros for example, may be displayed on the display terminal 14 or optional hard copy device 15, and the information may be permanently stored, along with other patient data, on the data storage device 16. In the preferred embodiment, permanent data storage is performed with a standard, commercially available disk drive.

Parametric modeling in frequency analyzer 10 of the heart sound signal 3 requires the selection of the appropriate model for the signal. The auditory component associated with coronary stenosis may be most appropriately expressed as a combination of several sinusoids buried in noise. In one embodiment the Autoregressive (AR) model is utilized in frequency analyzer 10 to evaluate and define the diastolic frequency spectrum of y(n). In other embodiments, different parametric models such as Moving Average (MA), Autoregressive Moving Average (ARMA), and Eigenvector methods may be employed to describe the frequency spectra associated with coronary stenosis.

Figure 4:
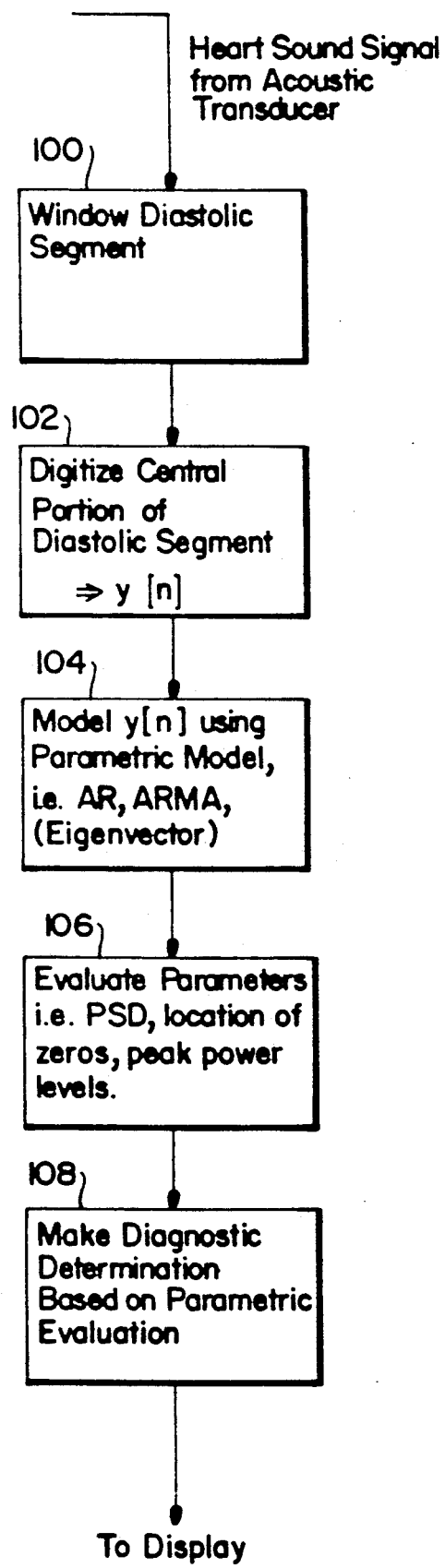
FIG. 4 is a block diagram of the parametric spectral analysis procedure of the present invention.

The parameter based decision criteria which may be employed by turbulent flow detector 12 for identifying those particular sounds associated with coronary stenosis include the power spectral density function, zeros of linear prediction coefficients, reflection coefficients, and peak power levels of the frequency spectrum of y(n). These decision criteria may be employed by turbulent flow detector 12 either separately, or in conjunction with one another for increased reliability in identifying the auditory component of interest Referring now to FIG. 4, shown is a block diagram of the parametric modeling and analysis procedure of the present invention. The heart sound signal 3 as recorded by the acoustic transducer 1 arrives at step 100 where the heart sound signal 3 is limited, by diastolic window section 9, to the diastolic segment of the signal 3. Next, either as part of the diastolic windowing process or as an additional step 102, the central portion of the diastolic segment is digitized to form y(n).

In an embodiment using the AR model, in step 104 the frequency analyzer 10 takes each of the digitized samples y(n) from the diastolic window section 9 and expresses each sample as a linear combination of previous samples and an error signal, e(n), and the error signal may be assumed to be independent of the previous samples $$\hat{y}(n) = \sum_{p=1}^{M} a_p \cdot y(n - p) + e(n)$$

where:
y(n) represents the diastolic heart sounds
$a_p$ represents the AR coefficients
e(n) represents the noise signal
M represents the model order The AR estimation of the power spectral density function is given by:

$$S_{yy}(w) = \frac{\sigma_e^2}{\left| 1 + \sum_{p=1}^{M} a_p e^{-jwp} \right|^2}$$

where
$\sigma_e^2$ is the noise variance and is assumed to be a constant.
w is the frequency.

Since $\sigma_e^2$ is a constant, the shape of the diastolic heart sound spectrum may be calculated within frequency analyzer 10 using only the AR prediction coefficients, $a_p$.

Methods for evaluating the AR model to solve for the prediction coefficients, $a_p$, are divided into two broad classifications: block processing and adaptive methods Thus, these model prediction coefficients can be calculated in frequency analyzer 10 either by using block processing methods which require the entire data segment be available for processing, or adaptive methods which operate on sequential data points. Popular examples of the former include autocorrelation, covariance, and Burg's (maximum entropy) methods, while adaptive techniques include the Least Mean Square (LMS), the conventional Recursive Least Square (RLS), and the adaptive lattice algorithms. An estimate of the power spectral density function can be determined from the prediction coefficients, and subsequently evaluated by turbulent flow detector 12.

Of the adaptive predictors, the simplicity of the LMS predictor underlies its wide acceptance, though the Gradient Adaptive Lattice (GAL) predictor, an adaptive version of Burg's method, is considered a better estimator because of faster convergence, improved numerical stability, and modular construction. Recent improvements in the fast RLS filters have reduced computational complexity and enhanced numerical stability. The Recursive Least Square Lattice (RLSL) is particularly appealing because of its excellent convergence and fast parametric tracking capabilities. Though computationally more complex, simulations have shown that its performance is generally better than gradient based algorithms. Additionally, RLSL algorithms, like gradient methods, are modular in form and insensitive to the eigenvalue spread of the correlation matrix of the input signal.

In the preferred embodiment, a block processing method is used in frequency analyzer 10 to determine the AR coefficients, specifically, the modified Yule-Walker method. This method is chosen since it provides a better estimate of the peak frequencies than the more traditional Maximum Likelihood methods when the signal contains narrow band information as is the case with diastolic heart sounds. In addition, such block processing methods are somewhat easier to implement in a fully automated system and provide performance equivalent to that of adaptive methods, provided, that the signal being analyzed can be assumed to be a stationary process as is the case with diastolic heart sounds.

In the preferred embodiment, the sample autocorrelation lags are first estimated in frequency analyzer 10 for a number of diastolic segments taken from individual cardiac cycles. Then, in conjunction with spectral and parameter averager 11, the averaged (optimal) autocorrelation lags are calculated from the individual lags and are used to construct the estimated autocorrelation matrix, R. From this averaged, estimated autocorrelation matrix R, the AR spectrum and the zeros of the AR prediction coefficients may be calculated by solving the modified Yule-Walker equations. This produces an AR model representation of the diastolic segment of a number of (10-40) individual cardiac cycles which may then undergo further analysis in the turbulent flow detector 12. In the preferred embodiment, the order, M, of the autocorrelation matrix, R, is taken as 7.

Figure 5:
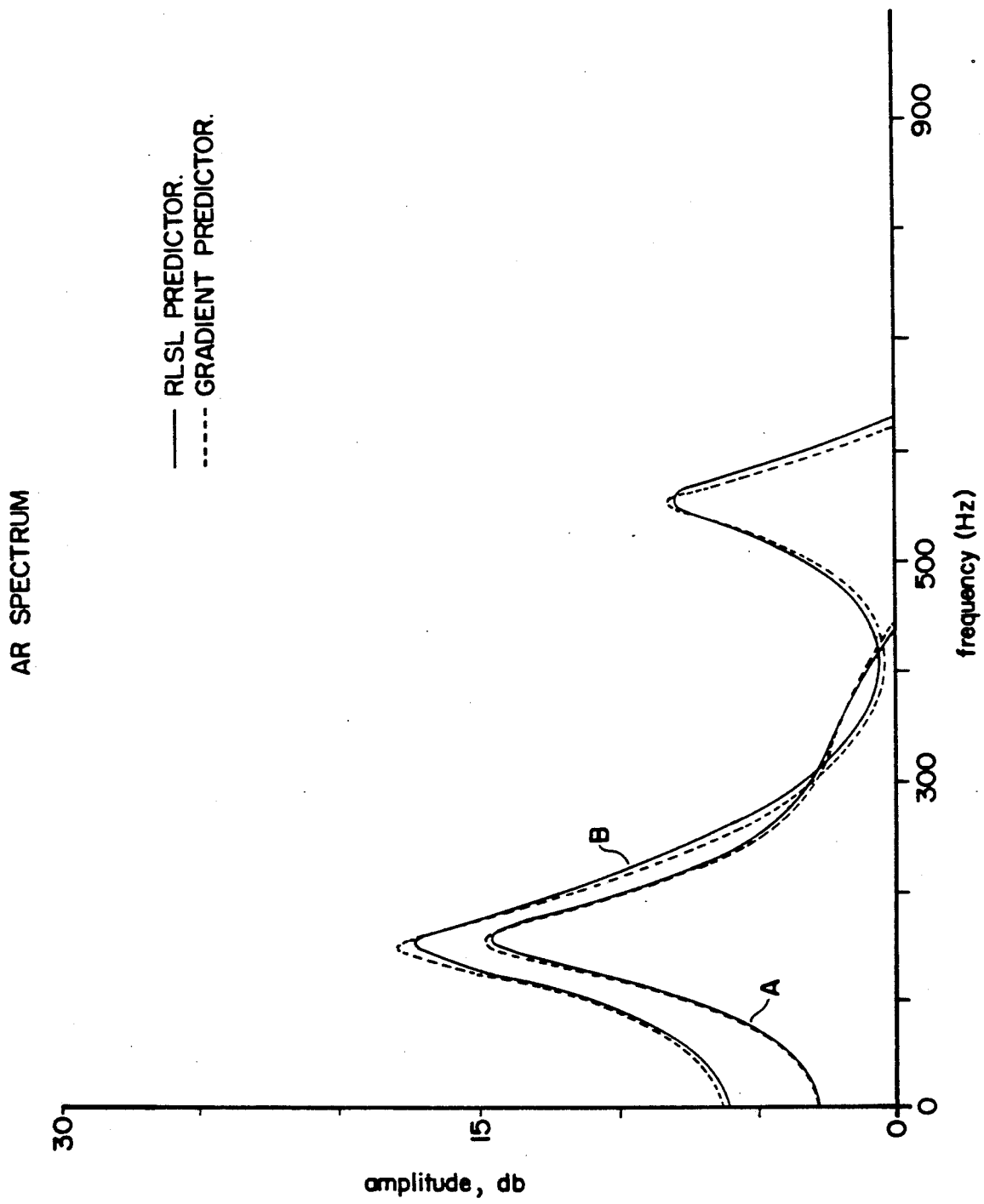
FIG. 5 shows diagrams of the averaged AR diastolic frequency spectra of a normal patient, A, and one with coronary artery disease, B, these diagrams being derived using equipment in accordance with the present invention.

Referring to FIG. 5, shown is the averaged AR spectra of y(n) for a normal patient A, and a diseased patient B. Comparing these spectra, diseased patients suffering from coronary stenosis typically have a higher percentage of spectral energy in the high frequency range (above approximately 300 Hz.) than do normal patients. This higher percentage in the high frequency range is attributable to the presence of the auditory component in the heart sound signal 3 due to coronary stenosis Patient A shows approximately 15% of the spectral energy above 300 Hz., whereas diseased patient B shows approximately 30% of the spectral energy above 300 Hz. Thus, in one embodiment the decision criterion employed by the turbulent flow detector 12 in step 106 (FIG. 4) may comprise calculating the power spectral density (PSD) above and below 300 Hz in the averaged diastolic frequency spectrum.

In another embodiment, different parametric characteristics of parametrically modeled y(n) could be utilized in step 106, either separately or in conjunction with one another, as a decision criterion to identify the turbulence associated with occluded coronary arteries. For example, the turbulent flow detector 12 may employ a decision criterion based on an estimation of the zeros of the adaptive filter coefficients of the AR model constructed by frequency analyzer 10 as detailed above. While the zeros are based on the same information as the power spectrum, they present the information in a different manner, specifically emphasizing the location and magnitude of spectral peaks. Predictably, all zeros of the inverse filter function, which are the same as the poles of the AR model transfer function, fall within the unit circle since the model transfer function is stable. There typically exists in all patients a large, relatively low frequency (50-300 Hz.) peak which gives rise to a complex conjugate pair of zeros falling close to the unit circle However, as determined using equipment in accordance with the present invention, second and third pairs of zeros typically vary in their position with respect to the unit circle in a manner related to the disease state. Usually the second, and frequently the third, complex conjugate pair of zeros fall farther from the unit circle in normal patients than those with coronary artery disease. The turbulent flow detector 12 evaluates the location of these pairs of zeros in step 106 and provides the appropriate diagnostic information in step 108 to the display device 13.

Another decision criterion employable by turbulent flow detector 12 is one which is based on the reflection coefficients obtained from parametrically modeled y(n). For example, it has been determined that the value of the third reflection coefficient relative to the first two for a patient suffering from coronary stenosis is significantly greater than that of a normal patient. Thus, turbulent flow detector 12 may evaluate the relative value of the third reflection coefficient in order to diagnose coronary artery disease.

In an alternative embodiment of the present invention, frequency analyzer 10 utilizes Eigenvector modeling methods in step 104. The digitized diastolic heart sound signal from step 102, y(n), is represented as a number of sinusoids along with background noise:

$$y(n) = \sum_{i=1}^{L} C_i e^{jw_i n} + v(n)$$

where:
  $C_i$ is the amplitude of components in the diastolic heart sound signal.
  $W_i$ is the frequency of components in this signal.
  L is the number of components.
  v(n) is the noise signal.

In one embodiment, frequency analyzer 10 in step 104 first determines the frequencies, $w_i$, of the component sinusoids after which the component power levels, $p_i$ ($= C_i^2$), are evaluated from the power matrix, P. Again, various methods may be used in the frequency analyzer 10 in step 104 to describe the spectrum, such as the Pisarenko (PSR), MUSIC and Minimum-Norm methods Summarizing these methods, the Pisarenko method uses only the eigenvector corresponding to the minimum eigenvalue to calculate the spectrum and occasionally this approach may produce spurious zeros. The MUSIC method eliminates these spurious zeros by averaging the spectra from all of the eigenvectors corresponding to the noise subspace. The Minimum-Norm method treats the problem of spurious zeros by forcing them inside the unit circle. From the frequency estimations provided by any one of these methods, the component power levels of the signal can be determined from the power matrix.

Figure 6:
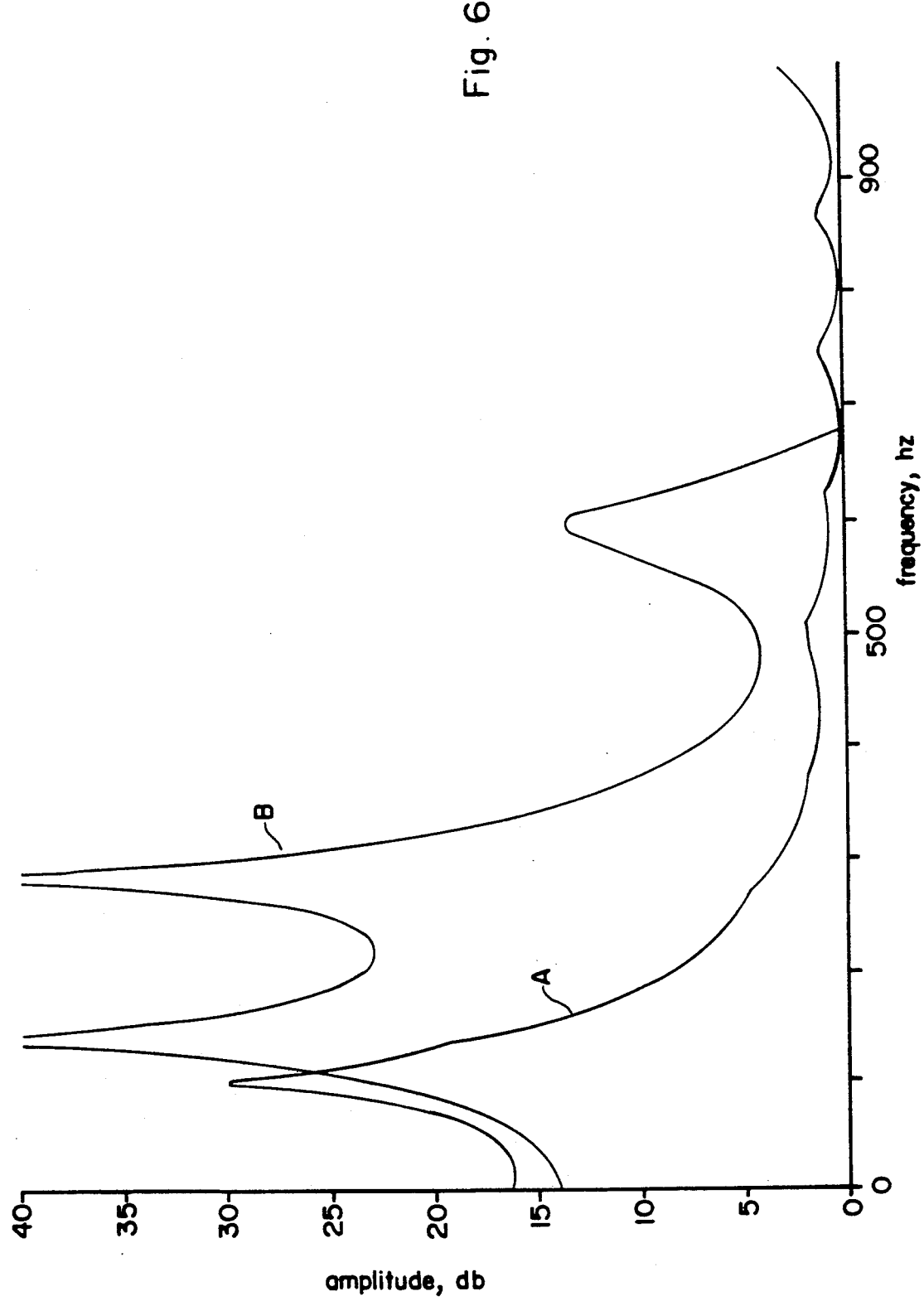
FIG. 6 shows diagrams of the averaged Eigenvector diastolic frequency spectra of a normal patient, A, and one with coronary artery disease, B, these diagrams being derived using equipment in accordance with the present invention.

In an embodiment in which the frequency analyzer 10 uses Eigenvector methods, in step 106 the turbulent flow detector 12 may employ decision criteria based on power levels, or alternatively, the relative location of zeros for the eigenfilter. FIG. 6 shows a typical spectra for a normal patient A and a diseased patient B using the Eigenvector and MUSIC methods. Both MUSIC and Minimun-Norm methods tend to produce similar spectral characteristics with nearly identical peak frequencies. FIG. 6 shows an obvious difference in the spectral characteristics between the normal A and diseased B patients. For the diseased patient B, the spectra typically contains two (or occasionally three) peaks, and the power level of the first peak is the greatest. In a patient A, the power level of the second peak (or occasionally, the third peak) decreases relative to the power level in the first peak In addition, the zeros of the eigenfilter are close to the unit circle for the diseased patient B, but move away from the unit circle for the normal patient A. Based on these known characteristics, in step 106 the turbulent flow detector 12 may apply the appropriate decision criteria and provide diagnostic information regarding coronary artery disease in a patient. In step 108, this diagnostic information is sent to the display device 13.

The entire diagnostic sequence of data collection analysis and display is automatically achieved by the sequence controller 17. In the preferred embodiment, the sequence controller is part of the signal processing microcomputer, although electronic timing hardware could also be used. Upon receiving a start command from the operator, the sequence controller 17 initializes the various signal processing stages 9, 10, and 11 and activates the diastolic section 9 which in turn initiates subsequent sections. After the averager 11 reports that 20-30 diastolic frequency spectra have been averaged, the sequence controller inactivates the diastolic section 9 and displays those results requested by the operator The sequence controller 17 can also interrupt the diagnostic sequence on operator command via the interrupt switch 19. Also, in the preferred embodiment the sequence controller performs error checking tasks, particularly the adequacy of the heart sound signal 3 and timing reference 6, both of which could be degraded by improper operator action. Internal performance checks along with calibration routines are also provided by the sequence controller 17.

Figure 7:
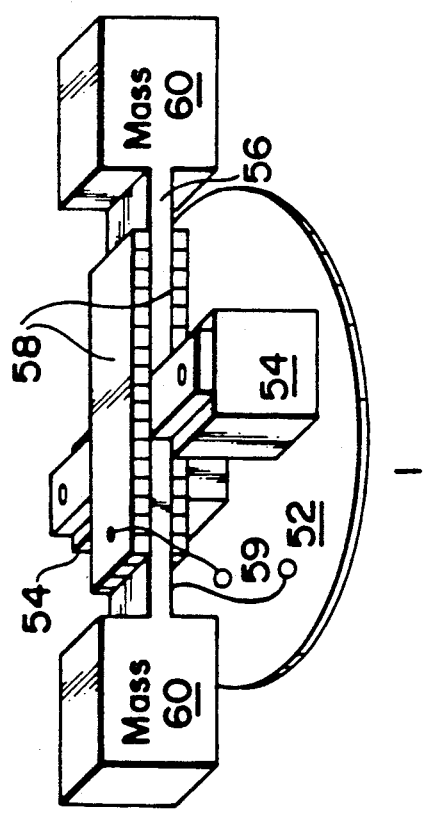
FIG. 7 shows a low mass accelerometer transducer in accordance with the present invention.

The present invention includes an acoustic transducer 1 for reliably detecting heart sounds in general, and more specifically, those turbulence sounds produced by coronary artery disease. FIG. 7 shows a low mass accelerometer transducer 1 capable of detecting low level heart sounds under very low signal to noise conditions. A contact plate 52 is mounted directly against the patients chest cavity. Chest vibrations caused by sounds within the chest cavity couple through to the contact plate 52 and frame structure 54 causing the cantilever beam structure 56 to bend in accordance with such vibrations.

Bending sensor elements 58 are attached to said cantilever beam 56 to produce an electrical output signal 59 representative of the chest vibrations. In the preferred embodiment a bending sensor 58 is attached to each side of the cantilever beam 56 so that when the structure bends, one sensor 58 is always in tension while the other is in compression. The output from each sensor 58 is added differentially together to form the output heart sound signal 59 of the transducer. For increased sensitivity, the beam 56 is weighted equally at both ends by mass 60.

The transducer has a resonant frequency slightly above 1200 Hz. which is found to increase sensitivity in the region of interest, that region being 300-1200 Hz. for diagnosing coronary stenosis. As explained above, the accurate detection of heart sounds including the range above 300 Hz is necessary in that the auditory component associated with coronary artery disease is expected to appear within this region.

The resonant frequency of transducer 1 is determined as a function of the thickness and length of the beam 56, and the mass of equal masses 60. The cantilever beam is constructed of aluminum; although alternatively other low mass, resilient materials may be utilized. The frame 54 and contact plate 52 are constructed of a rigid material capable of coupling the abovementioned chest vibrations to the beam 56. The bending sensors 58 are constructed of piezoceramic material and may be affixed to the beam using conductive epoxy. Optimally, the entire transducer apparatus provides very light loading to the chest and will weigh approximately 3.5 grams.

As discussed above, the present invention analyzes primarily the diastolic portion of the cardiac cycle. In order to locate and isolate this diastolic segment, time windowing of the heart sound signal 3 is employed. One manner of such windowing involves diastolic identification section 8 identifying the onset of diastole by delaying from the timing reference 6. For example, a delay between 350 to 550 msec., depending on the heart rate, from the R wave of the QRS timing reference 6 may be used to provide an indication of the onset of diastole. Diastolic window section 9 then causes 638 msec. of the heart sound signal 3 within that diastolic segment to be digitized as a preliminary data window for subsequent processing. In the preferred embodiment, an electro-optical pulse detector 4 located on the finger of the patient provides a signal indicating the occurrence of a pulse. Diastolic identification section 8 delays 100 msec. from this timing reference 6, in order to provide an indication of the onset of diastole, from which diastolic window section 9 subsequently causes 638 msec of the heart sound signal 3 within that diastolic segment to be digitized as the preliminary data window.

FIG. 8 shows the preferred embodiment of the present invention utilizing an automatic diastolic window placement and editing technique in diastolic window section 9. The signal representing the delayed timing reference as discussed above is received at step 200 in diastolic window section 9. In step 200, upon receipt of the delayed timing reference, a preliminary data window is established in the heart sound signal 3 from which the exact positioning of the diastolic window is subsequently determined. It is also within this preliminary data window that the heart sound signal 3 is evaluated for artifacts. In the preferred embodiment, the preliminary data window established in step 200 has a width of 638 msec and is delayed by the delayed timing reference and positioned 100 msec from the detection of a pulse.

It is noted that in the preferred embodiment, evaluation of the preliminary data window in order to establish the diastolic window is performed after the heart sound signal 3 has been bandpass filtered for the 20-100 Hz range. The characteristic frequency range of second heart sound S2 is between 20-100 Hz. Therefore, in order to avoid mistaking a burst of noise as S2, such bandpass filtering is preferred.

The preliminary data window comprises three evaluation zones of equal width, and the predetermined width of the preliminary data window must be sufficient to include the expected occurrence of the second heart sound S2 (as indicated by the delayed timing reference 6) and the succeeding first heart sound S1. Using a width of 638 msec, the first zone encompasses the expected location of the trailing edge of the second heart sound S2 and the third zone encompasses the expected location of the leading edge of the succeeding first heart sound S1. The second, or middle zone of the preliminary data window, is therefore approximately centered in the diastolic segment of the heart sound signal 3 for each cardiac cycle.

Also in step 200, threshold levels S2level1 and S2level2 are set in the preliminary data window. These threshold levels, as explained below, are used for discriminating the occurrence of second heart sound S2. In the preferred embodiment, S2level2 is equal to 0.75*S2level1 and S2level1 is set to the maximum value.

In step 202, a test window having a width of 12.5 msec is positioned within the preliminary data window adjacent the leading edge. The test window is used for calculating the RMS value of the heart sound signal within the test window in order to determine if the RMS value within exceeds that of the threshold S2level2.

In step 204, the signal processing means in section 9 progressively increment the test window position through the remainder of zones 1, 2 and 3. With each increment in step 204, the RMS value of the heart sound signal 3 within the test window is computed with reference to the test window position. Then in step 206, those computed values which exceed the S2level2 RMS threshold value are compiled into a group $R_y$, and corresponding test window positions are compiled into a group $R_x$, such that $$R_y = \{rms1, rms2, ...\} \quad R_x = \{x1, x2, ...\}$$

where x1, x2, ... are possible S2 (or S1) locations.

Next in step 208, section 9 processing means evaluate the elements in $R_x$ in order to establish a set of boundaries for the diastolic portion of the heart cycle. These boundaries provide both a reference for positioning of the diastolic window for subsequent analysis in the frequency analyzer 10, and for evaluating the record for artifacts. Accordingly, if all $X_i$ in $R_x$ fall in zone 1 and/or zone 3, then the following boundaries are set:

$b_l = \max \{(x1, x2, ...)\}$ evaluated over those values of $x_i$ in zone 1;

$b_h = \min \{(x1, x2, ...)\}$ evaluated over those values of $x_i$ in zone 3.

In this manner, the first third of the preliminary data window (zone 1) is searched using the test window for a segment whose RMS value exceeds the threshold. The position of the last segment in zone 1 which exceeds the threshold S2level2 determines the position of diastolic boundary $b_l$. Similarly, the last third of the preliminary data window (zone 3) is searched for the position of the first segment whose RMS value exceeds the threshold S2level2, this position determining the position of diastolic boundary $b_h$.

Signal processing means in diastolic window section 9 next determine in step 210 whether $|b_h - b_l| \geq$ diastolic window size (DW), and if that be the case, the diastolic window for subsequent analysis is positioned at:

$$\text{window pos} = b_l + \tfrac{1}{2}(b_h - B_l - DW)$$

where: DW = 256 msec. in the preferred embodiment so as to provide a diastolic window length of adequate size for subsequent parametric modeling in frequency analyzer section 10.

In step 212, the diastolic window section 9 evaluates whether artifacts are present within the diastolic window as positioned in step 210. If artifacts are determined to be present, diastolic window section 9 rejects that particular record. One artifact evaluation criterion in step 212 is if all $x_i$ in $R_x$ do not fall within zone 1 and/or zone 3. This would indicate the presence of an artifact during diastole, possibly due to breath sounds, stomach growls, external noise, etc. The record would therefore be rejected. Another criterion for rejecting a particular record in step 212 is if $|b_h - b_l| < DW$, thus indicating that the probable presence of an artifact has prohibited a diastolic window period of adequate size. An additional criterion is if some of the RMS values calculated within the diastolic window are very small (close to zero). In this case, the record is rejected due to probable microphone/transducer saturation.

Another criterion for detecting artifacts is if in zone 2, the heart sound signal 3 level exceeds or equals S2level2 This criterion serves in rejecting artifacts due to noise bursts.

A more advanced decision criterion, such as a square deviation test, may also be used to evaluate the diastolic window segment for the presence of artifacts. The heart sound signal data within the diastolic window consists of a data sequence, $D_w$, comprising a relatively large number of data samples, $N_w$. In the preferred embodiment, $N_w = 1024$. According to the central limit Theorem, this data sequence $D_w$ can be assumed to have a gaussian distribution which is determined by two parameters: mean value u and standard deviation $\sigma$.

In performing the F distribution test, reference parameters in the preferred embodiment are set in step 212 such that $u_o = 0$
$\sigma_o = 15\% * (S2level2).$ Next, the statistic F is defined by $$F = \frac{f_1}{f_2} = (N_w - 1)\frac{\mu^2 - \sigma_o^2}{\sigma^2 - \sigma_o^2}$$

which is proportional to $F(1, N_w-2)$
where:
$\mu$ and $\sigma$ are the mean value and standard deviation of $D_w$, respectively;
$f_1$ represents the square deviation difference between $D_w$ and the reference sequence from which $\sigma_o$ is calculated,
$f_2$ represents square deviation due to random effects.

From this equation, the value of F may be calculated in step 212 from each sample in $D_w$. Next, with predetermined 1 and $N_w-2$ degrees of freedom, and a significance level of 0.05, the value of F is obtained from an F-distribution table such that F satisfies:

$$\int_F^a F(1, N_w - 2)\, dv = a$$

where because $N_w$ is very large, $N_w-2$ may be treated as $\alpha$.

Therefore, if $F < F_\alpha$ then $u = u_o$ is true and the record of the diastolic window is accepted If $F \cdot F_\alpha$, then the F-test fails and the record is rejected.

Although particular embodiments of the present invention have been illustrated and described, other variations and modifications to the invention will be apparent to those skilled in the art from the foregoing disclosure and teachings. It is therefore understood that, within the scope of the appended claims, the invention may be practiced otherwise than as specifically described. Thus, while only certain embodiments of the invention have been specifically described herein, it will be apparent that numerous modifications may be made thereto without departing from the spirit and scope of the invention.

What is claimed is:

1. A low mass accelerometer transducer apparatus having increased sensitivity at high frequencies for detecting low level heart sounds in a noninvasive diagnostic system for coronary artery disease, said apparatus comprising:
   a double cantilever beam configuration, the unsupported end of each beam having an equal mass attached thereto;
   a bending moment sensor affixed to one side of said beam which produces an electrical output signal in relation to its bending moment;
   support means for supporting said beam;
   a contact plate affixed to said support means, for mounting against a patient's chest such that chest vibrations couple through said contact plate and support means causing said beam to bend in accordance with such vibrations; and
   the transducer having a resonant frequency at slightly above 1200 Hz and increased sensitivity in the frequency band of 300 to 1200 Hz.

2. An apparatus as defined in claim 1 which further comprises a bending moment sensor on the opposite side of said beam such that when said beam bends, one bending moment sensor will be in tension while the other will be in compression.

3. An apparatus as defined in claim 2 wherein the reference signals from each sensor are differentially added together for increased sensitivity.

4. An apparatus as defined in claim 1 wherein said bending moment sensor comprises a piezoceramic thin sheet.

* * * * *